(12) United States Patent
Zhao et al.

(10) Patent No.: US 9,457,187 B2
(45) Date of Patent: Oct. 4, 2016

(54) SYSTEMS AND METHODS FOR DELIVERING VAGAL NERVE STIMULATION

(71) Applicant: Cardiac Pacemakers, Inc., St. Paul, MN (US)

(72) Inventors: Weiying Zhao, Cupertino, CA (US); Quan Ni, Shoreview, MN (US); Stephen B. Ruble, Lino Lakes, MN (US); Jason J. Hamann, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/743,344

(22) Filed: Jun. 18, 2015

(65) Prior Publication Data

US 2015/0283380 A1    Oct. 8, 2015

Related U.S. Application Data

(63) Continuation of application No. 14/151,302, filed on Jan. 9, 2014, now Pat. No. 9,061,136, which is a continuation of application No. 13/796,401, filed on Mar. 12, 2013, now Pat. No. 8,630,707, which is a (Continued)

(51) Int. Cl.
*A61N 1/00* (2006.01)
*A61N 1/36* (2006.01)
(Continued)

(52) U.S. Cl.
CPC ......... *A61N 1/36114* (2013.01); *A61N 1/0551* (2013.01); *A61N 1/36053* (2013.01); *A61N 1/36592* (2013.01); *A61N 1/3712* (2013.01); *A61N 1/36117* (2013.01)

(58) Field of Classification Search
CPC .......... A61N 1/0551; A61N 1/36053; A61N 1/36114; A61N 1/36117; A61N 1/36592; A61N 1/3712
See application file for complete search history.

(56) References Cited

U.S. PATENT DOCUMENTS 5,330,507 A   7/1994 Schwartz
6,622,041 B2  9/2003 Terry, Jr. et al.
(Continued)

FOREIGN PATENT DOCUMENTS

AU   2012261486 B2   6/2014
CN   102143780 B     3/2014
(Continued)

OTHER PUBLICATIONS

"U.S. Appl. No. 12/487,266, Non Final Office Action Mailed Aug. 31, 2011", 6 pgs.
(Continued)

*Primary Examiner* — George Manuel
(74) *Attorney, Agent, or Firm* — Schwegman Lundberg & Woessner, P.A.

(57) ABSTRACT

According to various method embodiments, a person is indicated for a therapy to treat a cardiovascular disease, and the therapy is delivered to the person to treat the cardiovascular disease. Delivering the therapy includes delivering a vagal stimulation therapy (VST) to a vagus nerve of the person at a therapeutically-effective intensity for the cardiovascular disease that is below an upper boundary at which upper boundary the VST would lower an intrinsic heart rate during the VST.

20 Claims, 10 Drawing Sheets

Related U.S. Application Data continuation of application No. 13/444,400, filed on Apr. 11, 2012, now Pat. No. 8,401,640, which is a continuation of application No. 12/487,266, filed on Jun. 18, 2009, now Pat. No. 8,160,701.

(60) Provisional application No. 61/079,001, filed on Jul. 8, 2008.

(51) Int. Cl.
    *A61N 1/365*      (2006.01)
    *A61N 1/37*      (2006.01)
    *A61N 1/05*      (2006.01)

(56) References Cited

U.S. PATENT DOCUMENTS

| | | |
|---|---|---|
| 6,961,618 B2 | 11/2005 | Osorio et al. |
| 7,444,184 B2 | 10/2008 | Boveja et al. |
| 7,778,711 B2 | 8/2010 | Ben-david et al. |
| 8,160,701 B2 | 4/2012 | Zhao et al. |
| 8,224,444 B2 | 7/2012 | Ben-david et al. |
| 8,401,640 B2 | 3/2013 | Zhao et al. |
| 8,600,505 B2 | 12/2013 | Libbus et al. |
| 8,600,521 B2 | 12/2013 | Armstrong et al. |
| 8,630,707 B2 | 1/2014 | Zhao et al. |
| 8,688,212 B2 | 4/2014 | Libbus et al. |
| 8,700,150 B2 | 4/2014 | Libbus et al. |
| 8,918,190 B2 | 12/2014 | Libbus et al. |
| 8,918,191 B2 | 12/2014 | Libbus et al. |
| 8,923,990 B2 | 12/2014 | Libbus et al. |
| 8,965,522 B2 | 2/2015 | Libbus et al. |
| 9,061,136 B2 | 6/2015 | Zhao et al. |
| 2003/0212440 A1 | 11/2003 | Boveja |
| 2005/0143779 A1 | 6/2005 | Libbus |
| 2006/0100668 A1 | 5/2006 | Ben-David et al. |
| 2006/0178703 A1 | 8/2006 | Huston et al. |
| 2008/0021504 A1 | 1/2008 | McCabe et al. |
| 2008/0051839 A1 | 2/2008 | Libbus et al. |
| 2008/0058874 A1 | 3/2008 | Westlund et al. |
| 2008/0147140 A1 | 6/2008 | Ternes et al. |
| 2009/0076561 A1* | 3/2009 | Libbus et al. .......... 607/11 |
| 2010/0010556 A1 | 1/2010 | Zhao et al. |
| 2010/0114227 A1 | 5/2010 | Cholette et al. |
| 2012/0197333 A1 | 8/2012 | Zhao et al. |
| 2013/0190835 A1 | 7/2013 | Zhao et al. |
| 2014/0128953 A1 | 5/2014 | Zhao et al. |

FOREIGN PATENT DOCUMENTS

| | | |
|---|---|---|
| JP | 2011527598 A | 11/2011 |
| JP | 2013248533 A | 12/2013 |
| WO | WO-2010005482 A1 | 1/2010 |

OTHER PUBLICATIONS

"U.S. Appl. No. 12/487,266, Notice of Allowance mailed Dec. 14, 2011", 5 pgs.

"U.S. Appl. No. 12/487,266, Response to Non Final Office Action Mailed Aug. 31, 2011", 10 pgs.

"U.S. Appl. No. 13/444,400, Notice of Allowance mailed Nov. 14, 2012", 8 pgs.

"U.S. Appl. No. 13/796,401, Non Final Office Action mailed Aug. 12, 2013", 7 pgs.

"U.S. Appl. No. 13/796,401, Notice of Allowance mailed Sep. 12, 2013", 6 pgs.

"U.S. Appl. No. 13/796,401, Response filed Aug. 28, 2013 to Non Final Office Action mailed Aug. 2013-Dec. 2013", 8 pgs.

"U.S. Appl. No. 14/151,302, Non Final Office Action mailed Nov. 7, 2014", 6 pgs.

"U.S. Appl. No. 14/151,302, Notice of Allowance mailed Feb. 20, 2015", 8 pgs.

"U.S. Appl. No. 14/151,302, Preliminary Amendment filed Feb. 4, 2014", 7 pgs.

"U.S. Appl. No. 14/151,302, Response filed Feb. 3, 2015 to Non Final Office Action mailed Nov. 7, 2014", 7 pgs.

"Australian Application Serial No. 2009269901, Office Action mailed Feb. 22, 2012", 2 pgs.

"Australian Application Serial No. 2009269901, Response filed Aug. 22, 2012 to First Examiners Report mailed Feb. 22, 2012", 6 pgs.

"Australian Application Serial No. 2012261486, First Examiner Report mailed Oct. 25, 2013", 3 pgs.

"Chinese Application Serial No. 200980134904.0, Office Action mailed Mar. 21, 2013", 14 pgs.

"Chinese Application Serial No. 200980134904.0, Office Action mailed Aug. 15, 2013", 7 pgs.

"European Application Serial No. 09788804.4, Examination Notification Art. 94(3) mailed Oct. 31, 2014", 6 pgs.

"International Application Serial No. PCT/US/2009/03645, International Search Report mailed Aug. 31, 2009", 5 pgs.

"International Application Serial No. PCT/US/2009/03645, Written Opinion mailed Aug. 31, 2009", 10 pgs.

"International Application Serial No. PCT/US2009/003645, International Preliminary Report on Patentability mailed Jan. 20, 2011", 10 pgs.

"Japanese Application Serial No. 2011-517399, Decision on Rejection mailed Jun. 11, 2013", With English Translation, 3 pgs.

"Japanese Application Serial No. 2011-517399, Office Action mailed Oct. 30, 2012", With English Translation, 8 pgs.

"Japanese Application Serial No. 2011-517399, Response filed Jan. 30, 2013 to Office Action mailed Oct. 30, 2012", With English Claims, 17 pgs.

"Japanese Application Serial No. 2013-190328, Office Action mailed Sep. 2, 2014", With English translation, 6 pgs.

Bernik, T. R., et al., "Pharmacological Stimulation of the Cholinergic Antiinflammatory Pathway", J. Exp. Med., 195(6), (2002), 781-788.

Borovikova, L. V., "Vagus nerve stimulation attenuates the systemic inflammatory response to endotoxin", Nature, 405(6785), (May 25, 2000), 458-462.

"European Application Serial No. 09788804.4, Summons to Attend Oral Proceedings mailed Nov. 17, 2015", 4 pgs.

\* cited by examiner

SYSTEMS AND METHODS FOR DELIVERING VAGAL NERVE STIMULATION

CLAIM OF PRIORITY

This application is a continuation of and claims the benefit of priority under 35 U.S.C. §120 to U.S. patent application Ser. No. 14/151,302, filed on Jan. 9, 2014, now U.S. Pat. No. 9,061,136, which is a continuation of and claims the benefit of priority under 35 U.S.C. §120 to U.S. patent application Ser. No. 13/796,401, filed on Mar. 12, 2013, now U.S. Pat. No. 8,630,707, which is a continuation of and claims the benefit of priority under 35 U.S.C. §120 to U.S. patent application Ser. No. 13/444,400, filed on Apr. 11, 2012, now U.S. Pat. No. 8,401,640, which is a continuation of and claims the benefit of priority under 35 U.S.C. §120 to U.S. patent application Ser. No. 12/487,266, filed on Jun. 18, 2009, now U.S. Pat. No. 8,160,701, which claims the benefit of U.S. Provisional Application No. 61/079,001, filed on Jul. 8, 2008, under 35 U.S.C. §119(e), each of which is hereby incorporated by reference herein in its entirety.

TECHNICAL FIELD

This application relates generally to medical devices and, more particularly, to systems, devices and methods for delivering vagal nerve stimulation.

BACKGROUND

Neural stimulation has been proposed as a therapy for a number of conditions. Examples of neural stimulation therapies include neural stimulation therapies for respiratory problems such as sleep disordered breathing, blood pressure control such as to treat hypertension, cardiac rhythm management, myocardial infarction and ischemia, heart failure (HF), epilepsy, depression, pain, migraines, eating disorders and obesity, and movement disorders.

Some neural stimulation therapies stimulate the vagus nerve to lower heart rate. For example, previously-proposed cardiovascular therapies use vagal stimulation therapy (VST) to lower heart rate, which has long been considered beneficial to HF patients, for example, based on the belief that a lower heart rate will reduce the oxygen demand of the heart, and improve profusion and work efficiency of the failing heart.

SUMMARY

According to various method embodiments, a person is indicated for a therapy to treat a cardiovascular disease, and the therapy is delivered to the person to treat the cardiovascular disease. Delivering the therapy includes delivering a VST to a vagus nerve of the person at a therapeutically-effective intensity for the cardiovascular disease that is below an upper boundary at which upper boundary the VST would lower an intrinsic heart rate during the VST. A non-exhaustive example of cardiovascular disease is heart failure. According to some embodiments, delivering the VST at a therapeutically-effective intensity for heart failure includes delivering the VST at an intensity to induce laryngeal vibration.

Some embodiments provide a method for operating an implantable medical device for delivering a therapy for a cardiovascular disease. VST is delivered with a VST intensity that is therapeutically-effective for the cardiovascular disease. Heart rate is sensed both before delivery of the VST and during delivery of the VST. If the heart rate sensed during delivery of the VST is less than the heart rate sensed before delivery of the VST by at least a threshold, the VST intensity is automatically reduced to a reduced VST intensity. The reduced VST intensity results in a difference between the heart rate sensed during delivery of the VST and the heart rate sensed before delivery of the VST that is less than the threshold. The VST is delivered with a reduced VST intensity that is therapeutically effective for the cardiovascular disease and that does not drive a lower intrinsic heart rate.

Various implantable system embodiments comprise a pulse generator adapted to deliver an electrical signal through the implantable electrodes to the vagus nerve to provide the VST at a programmed intensity. The electrical signal has programmed parameters to provide the VST at the programmed intensity selected to provide therapeutically beneficial stimulation for the cardiovascular disease without substantially reducing an intrinsic heart rate of the patient during the VST in comparison to the intrinsic heart rate of the patient before the VST.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
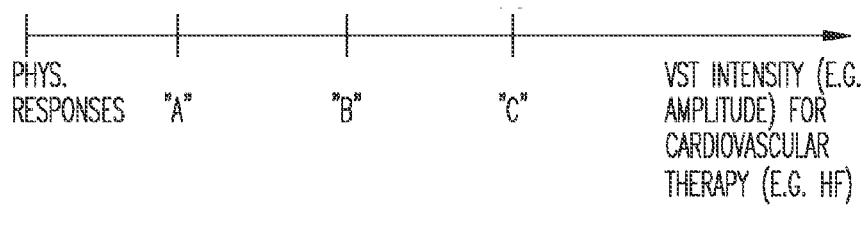
FIG. 1 illustrates increasing VST intensity from the left side to the right side of the figure, and further illustrates intensity thresholds that elicit various physiological responses to VST.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

Stimulating the sympathetic and parasympathetic nervous systems can cause heart rate, blood pressure and other physiological responses. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

A reduction in parasympathetic nerve activity contributes to the development and progression of a variety of cardiovascular diseases. The present subject matter can be used to prophylactically or therapeutically treat various cardiovascular diseases by modulating autonomic tone. Examples of such diseases or conditions include HF, hypertension, and cardiac remodeling. These conditions are briefly described below.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have reduced autonomic balance, which is associated with LV dysfunction and increased mortality.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Vagal stimulation therapy (VST) provides an exciting opportunity to treat various cardiovascular diseases, including HF. However, VST-induced bradycardia could cause symptomatic side effects for HF patients, especially during exercise, and could provide undesired inotropic and dromotropic effects. Our research suggests that the beneficial effects of VST on cardiac function and remodeling are not necessarily mediated via heart rate reduction. That is, VST can benefit HF patients without the undesired chronotropic effects associated with VST as well as other side effects due to high intensity stimulation such as coughing, etc. Rather, anti-inflammatory, anti-sympathetic, and anti-apoptosis mediators are triggered at lower VST intensities than intensities at which a heart rate reduction is realized. These mediators function as pathways through which the VST provides the therapeutic effects for cardiovascular disease.

Vagal nerve signaling plays an important role in modulating systemic inflammatory response and apoptosis, which are important in the development and progression of HF. Low level of efferent vagal nerve stimulation (1 Hz) has been shown to attenuate the release of proinflammatory cytokines (such as tumor necrosis factor, interleukin, etc.) from macrophage through nicotinic acetylcholine receptors (see Borovikova, L V. Nature. 2000, 405: 458-462). Our internal preclinical data suggests that the therapeutic level of VST could modulate inflammatory and apoptosis signaling pathways without lowering heart rate. The preclinical studies used a neural stimulator prototype to deliver VST that non-selectively stimulates both afferent axons and efferent axons in the vagus nerve according to a predetermined schedule for the VST.

As disclosed herein, various embodiments deliver therapeutically-effective doses of VST non-selectively to afferent and efferent axons at low levels to avoid or inhibit bradycardia responses induced by stimulation of the vagus nerve. The VST is delivered with a reduced VST intensity that is therapeutically effective for the cardiovascular disease and that does not drive a lower intrinsic heart rate. That is, heart rate is maintained during VST without resort to bradycardia support pacing of the myocardium during VST. Described herein are methods, systems and apparatus to deliver VST therapy. According to various embodiments, heart rate is monitored, and VST is adjusted to appropriately avoid or reduce the heart rate reduction effects of vagal stimulation. For example, if the heart rate drops to a certain level during VST, the parameter setting would be adjusted to reduce VST dose for the next VST stimulus. VST is delivered with a therapeutically-effective dose to achieve its beneficial effects on autonomic function without significant chronotropic side effects, improving the tolerability of this VST.

The vagus nerve is a complex physiological structure with many neural pathways that are recruited at different stimulation thresholds. Various physiological responses to vagal stimulation are associated with various thresholds of VST intensity.

For example, FIG. 1 illustrates increasing VST intensity from the left side to the right side of the figure, and further illustrates intensity thresholds that elicit various physiological responses to VST. VST causes a physiological response "A" at a lower intensity than an intensity at which VST causes a physiological response "B", which occurs at a lower VST intensity than an intensity at which VST causes a physiological response "C". Stated another way, VST has to reach a certain level before triggering response "A," and has to reach higher levels to trigger responses "B" and "C".

The physiological responses at the lower VST intensities have therapeutically-effective results for cardiovascular diseases such as HF. These responses mediate or provide pathways for these therapies. Examples of such responses that are beneficial for HF at the lower VST intensities include anti-inflammation, anti-sympathetic, and anti-apoptosis responses, and an increased NO. The physiological responses at the higher VST intensities may not be desirable. Examples of responses to higher VST intensities that may reduce the ability of the patient to tolerate VST include, but are not limited to, reduced heart rate, prolonged AV conduction, vasodilation, and coughing.

The intensity of the VST can be adjusted by adjusting parameter(s) of the stimulation signal. For example, the amplitude of the signal (e.g. current or voltage) can be increased to increase the intensity of the signal. Other stimulation parameter(s) can be adjusted as an alternative to or in addition to amplitude. For example, stimulation intensity can vary with the frequency of the stimulation signal, a stimulation burst frequency, a pulse width and/or a duty cycle.

Figure 2:
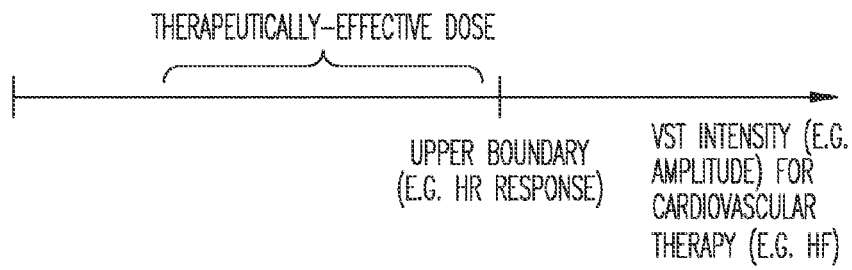
FIG. 2 illustrates increasing VST intensity from the left side to the right side of the figure, and further illustrates an intensity threshold that elicits an undesired physiological response to VST, such as a reduced heart rate response to VST, that is used to define an upper boundary for the VST intensity.

FIG. 2 illustrates increasing VST intensity from the left side to the right side of the figure, and further illustrates an intensity threshold that elicits an undesired physiological response to VST, such as a reduced heart rate response to VST, that is used to define an upper boundary for the VST intensity. For an open loop VST system, heart rate is monitored during VST testing. This VST testing may be based on a relatively large human population to determine the heart rate threshold. The VST testing may also be performed during the implantation procedure, using a process that verifies capture of the vagus nerve using observed heart rate reduction, that determines the intensity threshold at which the heart rate reduction is observed, and that uses the intensity threshold to provide an upper boundary or otherwise set the VST intensity below the heart rate threshold. Another VST testing example that may be performed during the implantation procedure verifies capture using another physiological response (e.g. laryngeal vibration sensed by sensors or by patient, detected nerve traffic, or other). The VST intensity can be set based on the intensity at which nerve capture was sensed (the intensity itself, a factor of the intensity, or an offset from the intensity).

Figure 3:
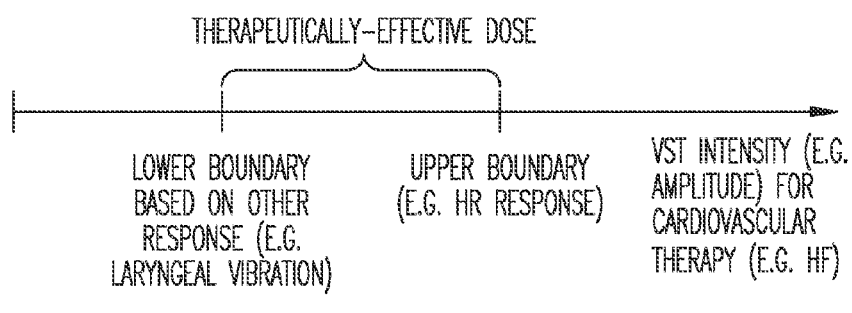
FIG. 3 illustrates increasing VST intensity from the left side to the right side of the figure, and further illustrates an intensity threshold that elicits an undesired physiological response to VST that is used to define an upper boundary for the VST intensity and another intensity threshold that elicits another physiological response to VST.

FIG. 3 illustrates increasing VST intensity from the left side to the right side of the figure, and further illustrates an intensity threshold that elicits an undesired physiological response to VST that is used to define an upper boundary for the VST intensity and another intensity threshold that elicits another physiological response to VST. For example, the VST intensity threshold for an undesired heart rate response can be used as an upper boundary, and the VST intensity threshold for a desired laryngeal vibration response can be used as a lower boundary. As illustrated in FIG. 3, preclinical studies indicate that laryngeal vibration is detected at a lower VST intensity threshold than the VST intensity threshold for eliciting the heart rate response. Some embodiments use laryngeal vibration as a lower boundary for VST.

Figure 4:
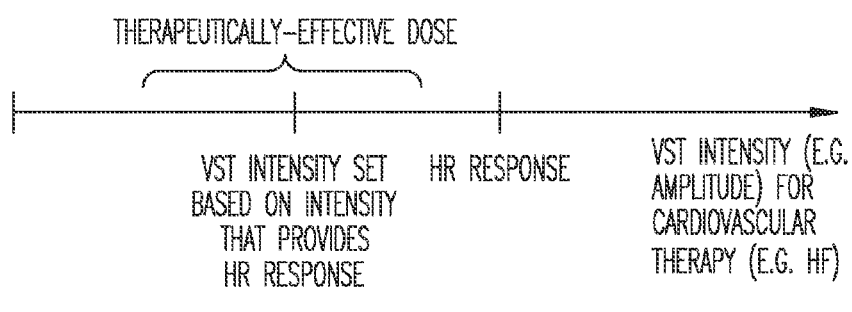
FIG. 4 illustrates increasing VST intensity from the left side to the right side of the figure, and further illustrates an intensity threshold that elicits an undesired physiological response to the VST that is used to set the VST intensity.

FIG. 4 illustrates increasing VST intensity from the left side to the right side of the figure, and further illustrates the intensity threshold that elicits an undesired physiological response to the VST that is used to set the VST intensity. For example, if a heart rate response is observed at VST intensity level "X", the therapeutically-effective intensity level for the VST can be set as a percentage of "X" (e.g. approximately 50% of "X") or as an offset "Z" from "X" (e.g. "X" less "Z").

Figure 5:
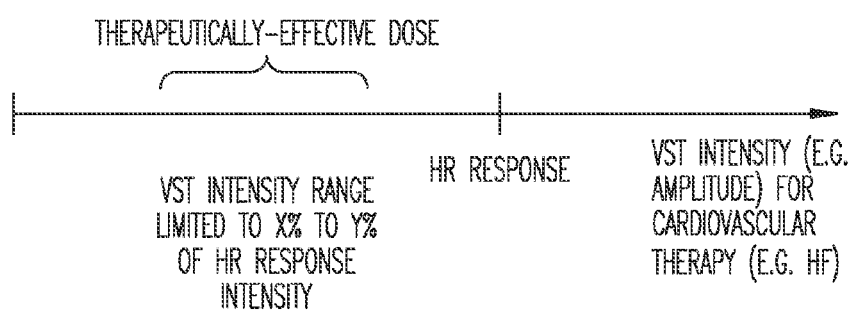
FIG. 5 illustrates increasing VST intensity from the left side to the right side of the figure, and further illustrates an intensity threshold that elicits an undesired physiological response to VST that is used to set an allowable range for the VST intensity.

FIG. 5 illustrates increasing VST intensity from the left side to the right side of the figure, and further illustrates an intensity threshold that elicits an undesired physiological response to VST that is used to set an allowable range for the VST intensity. For example, if a heart rate response is observed at VST intensity level "X", the therapeutically-effective intensity level for VST can be set using percentages of "X" (e.g. Y1% to Y2% of "X") or using offset(s) "Z1" and/or "Z2" from "X" for at least one of the beginning of the allowable range of intensities or the end of the allowable range of intensities.

The therapeutic efficacy of the VST can be assessed acutely (e.g. within seconds or minutes) such as may be beneficial for a closed loop system or during an implantation procedure, and can be assessed on a longer term basis (e.g. on the order of hours, days, weeks, and months) such as may be beneficial to provide follow-programming updates for either open loop or closed loop systems. Examples of acute markers which could be measured to tell if the dose is in the therapeutic effective range include anti-inflammatory cytokines and autonomic balance markers. Examples of anti-inflammatory cytokines include serum TNF-alpha, IL-1, IL6, etc. Examples of autonomic balance markers include plasma NE (an indicator of sympathetic tone), heart rate variability (HRV) and heart rate turbulence (HRT). Longer term assessment of therapeutic efficacy can be determined using various methods currently used to monitor the progression of heart failure (e.g. electrogram readings and various measures of cardiac output, contractility, and size of the left ventricle). Other physiological responses that in and of themselves are not beneficial for the therapy, such as laryngeal vibration, may be used if their response threshold has a known relationship to trigger desired mediators (e.g. mediators, anti-apoptosis mediator, and anti-sympathetic) through which the applied VST provides effective therapy for the cardiovascular disease.

Figure 6:
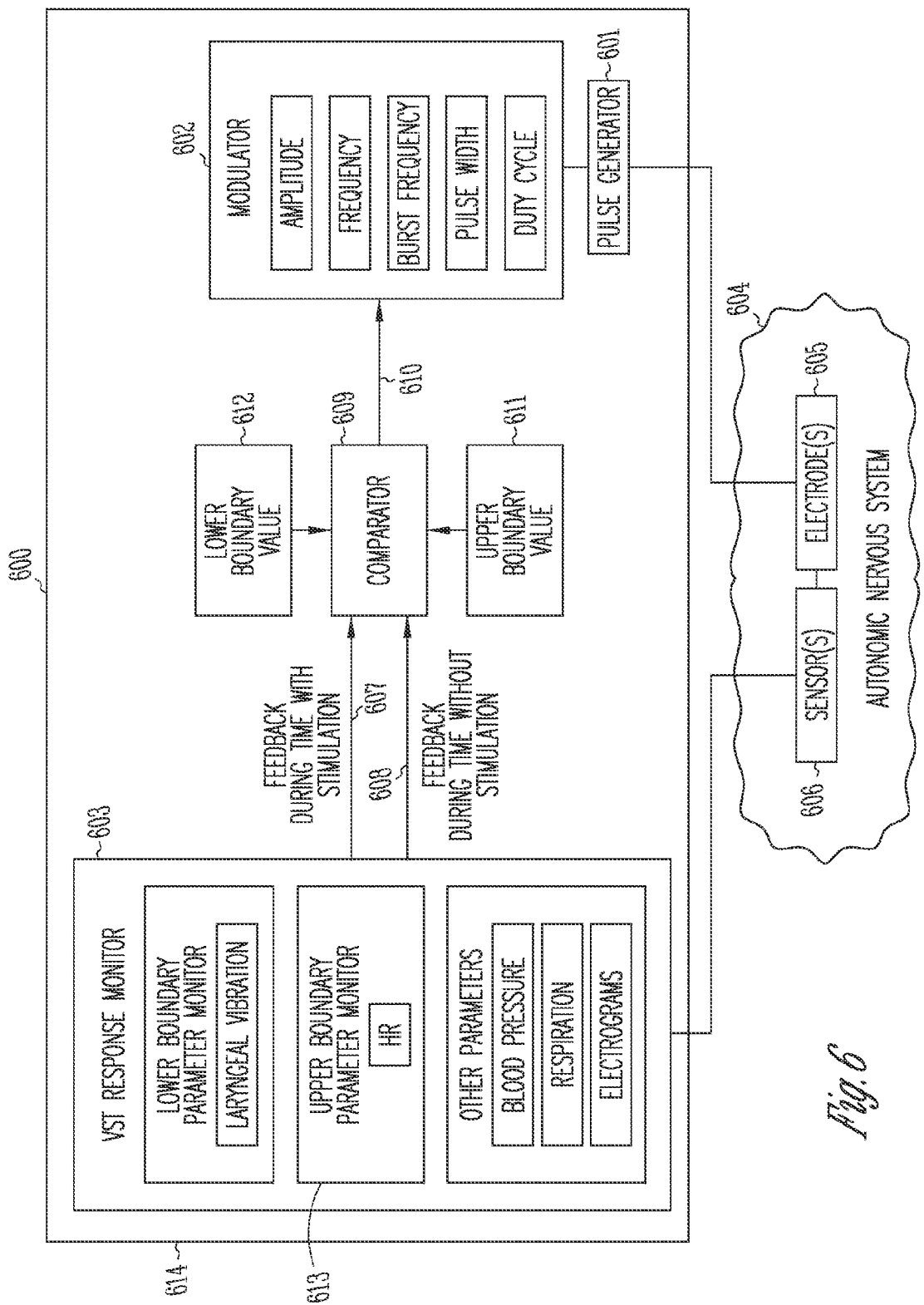
FIG. 6 illustrates an embodiment of a VST system.

FIG. 6 illustrates a VST system, according to various embodiments. An implantable device may provide the entire VST system. Some embodiments use external devices to provide the monitoring functions, such as during implantation of an implantable vagus nerve stimulator. The illustrated VST system 600 includes a pulse generator 601 to provide VST, a modulator 602 to change or modulate intensity of the VST, and a VST response monitor 603 to provide feedback. The autonomic nervous system is generally illustrated at 604. Appropriate electrode(s) 605 are used to provide desired neural stimulation and sensor(s) 606 to sense a parameter that is affected by the neural stimulation. Physiological parameter(s) that quickly respond to VST can be used in closed loop systems or during the implantation process. Examples of such parameters include heart rate, laryngeal vibration, blood pressure, respiration, electrogram parameters. Other cardiovascular parameter(s) and other surrogate parameters that have a quick and predictable response indicative of the overall response of the parasympathetic nervous system to the neural stimulation. Other parameter(s) that have a slower response may be used to confirm that a therapeutically-effective dose is being delivered. The sensor(s) and electrode(s) can be integrated on a single lead or can use multiple leads. Additionally, various system embodiments implement the functions illustrated in FIG. 6 using an implantable neural stimulator capable of communicating with a distinct or integrated implantable cardiac rhythm management device.

The illustrated monitor 603 monitors the parameter during a time with stimulation to provide a first feedback signal 607 indicative of a parameter value corresponding to a time with stimulation and during a time without stimulation to provide a second feedback signal 608 indicative of a parameter value corresponding to a time without stimulation. The signals 607 and 608 are illustrated as separate lines. These signals 607 and 608 can be sent over different signal paths or over the same signal path. A comparator 609 receives the first and second feedback signals 607 and 608 and determines a detected change in the parameter value based on these signals. Additionally, the comparator compares the detected change with an allowed change, which can be programmed into the device. For example, the device can be programmed to allow a heart rate reduction during VST to be no less than a percentage (e.g. on the order of 95%) of heart rate without stimulation. The device may be programmed with a quantitative value to allow a heart rate reduction during VST to be no less than that quantitative value (e.g. 5 beats per minute) than heart rate without stimulation.

The illustrated device is programmed with an upper boundary value 611 corresponding to a monitored parameter value used to provide an upper boundary on VST intensity, and the VST response monitor 603 includes an upper boundary parameter monitor 613. The upper boundary parameter monitor provides a signal indicative of a sensed value for the parameter, which is compared to the upper boundary value. The VST intensity is adjusted to be below the upper VST intensity, as detected using the upper boundary value and upper boundary parameter monitor. The upper boundary value may be pre-programmed based on patient-specific responses to VST or based on data for a patient population. The illustrated embodiment monitors heart rate, and compares sensed heart rate to a preprogrammed heart rate corresponding to an upper boundary for VST intensity.

The illustrated device may also be programmed with a lower boundary value 612 corresponding to a monitored parameter value used to provide a lower boundary on VST intensity, and the VST response monitor 603 includes a lower boundary parameter monitor 614. The lower boundary parameter monitor provides a signal indicative of a sensed value for the parameter, which is compared to the lower boundary value. The VST intensity is adjusted to be above the lower VST intensity, as detected using the lower boundary value and lower boundary parameter monitor. The lower boundary value may be pre-programmed based on patient-specific responses to VST or based on data for a patient population. The illustrated embodiment monitors laryngeal vibration.

Some embodiments use a therapy protocol that adjusts the VST intensity, limited by the upper boundary for the VST intensity and in some embodiments by the lower boundary for the VST intensity. The VST intensity can be adjusted, within the allowed bounds set by the present subject matter, based on other parameters such as blood pressure, respiration, and electrogram measurement. Some therapy protocols adjust the upper boundary and/or lower boundary for VST intensity based on a schedule (e.g. time of day) or sensed data (e.g. activity).

A comparison of the detected change (based on signals 607 and 608) and the allowed change provide a comparison result 610, which is used to appropriately control the modulator to adjust the applied VST.

Various modulator embodiments adjust VST intensity by changing an amplitude of a stimulation signal used to provide VST, by changing a frequency of a stimulation signal used to provide VST, by changing a burst frequency of a stimulation signal used to provide VST, by changing a pulse width of a stimulation signal used to provide VST, by changing a duty cycle of a stimulation signal used to provide VST, or various combinations of two or more of these stimulation signal characteristics.

The illustrated system for delivering VST is useful in extended therapy applications. Examples of extended therapy applications involve applying stimulation to prevent remodeling of cardiac tissue and to reverse remodel cardiac tissue in cardiovascular disease. VST can be applied for a portion (approximately 10 seconds) of each minute, for example. A VST dose may be adjusted by adjusting the duration or duty cycle of the stimulation (e.g. approximately 5 seconds or 15 seconds each minute or approximately 5 to 15 seconds every 30 seconds or approximately 5 to 30 seconds every 2 minutes, or approximately 5 seconds to 3 minutes every 5 minutes or a continuous stimulation). According to an embodiment, the VST non-selectively stimulates both efferent and afferent axons. The illustrated values are provided by way of example, and not limitation. Over the course of days, weeks, months and years, the physiological response to VST can vary for a number of reasons, such as nerve adaptation, tissue encapsulation, fibrosis, impedance changes, and the like. Various closed loop system embodiments monitor at least one parameter that has a quick and predictable response to VST, and uses the monitored parameter to appropriately change the neural stimulation signal to result in a desired stimulation of the parasympathetic nervous system. Some embodiments monitor heart rate, and adjust VST intensity to avoid affecting heart rate with VST. Some embodiments monitor laryngeal vibration, and adjust VST intensity as necessary for the VST to elicit laryngeal vibration.

Open loop VST systems set the VST intensity to avoid or reduce heart rate effects of VST. For an open loop VST system, heart rate is monitored during VST testing. This VST testing may be based on a relatively large human population to determine the heart rate threshold. The VST testing may also be performed during the implantation procedure, using a process that verifies capture of the vagus nerve using observed heart rate reduction, that determines the intensity threshold at which the heart rate reduction is observed, and that uses the intensity threshold to provide an upper boundary or otherwise set the VST intensity below the heart rate threshold. According to some embodiments, a lower boundary for the VST intensity can be set during the implantation process. For example, laryngeal vibration is felt by the patient or sensed by a sensor such as an accelerometer at a VST intensity level below the VST intensity level where a heart rate effect is detected. A combination of parameter settings is chosen to avoid any significant bradycardia effects. Some embodiments avoid any bradycardia effects. Some embodiments allow a relatively insignificant amount of heart rate slowing (e.g. heart rate during VST at 95% of heart rate without VST). The upper boundary for the VST intensity is based on the allowed heart rate change caused by VST from the intrinsic heart rate without VST.

By way of example, VST intensity for an open loop system may be titrated as follows. When VST is turned on for the first time, the heart rate is monitored during testing. If there is any significant bradycardia during the ON time of VST cycle, VST intensity (also referred to as VST dose) will be reduced. The VST dose can be reduced by adjusting one or more VST parameters such as amplitude, frequency, pulse width, etc. During the follow-up office visits for therapy titration, VST parameters may be adjusted to provide a therapeutically-effective dose without significant bradycardia effects. The limit for bradycardia is predetermined (the degree of bradycardia permitted during VST).

Figure 7:
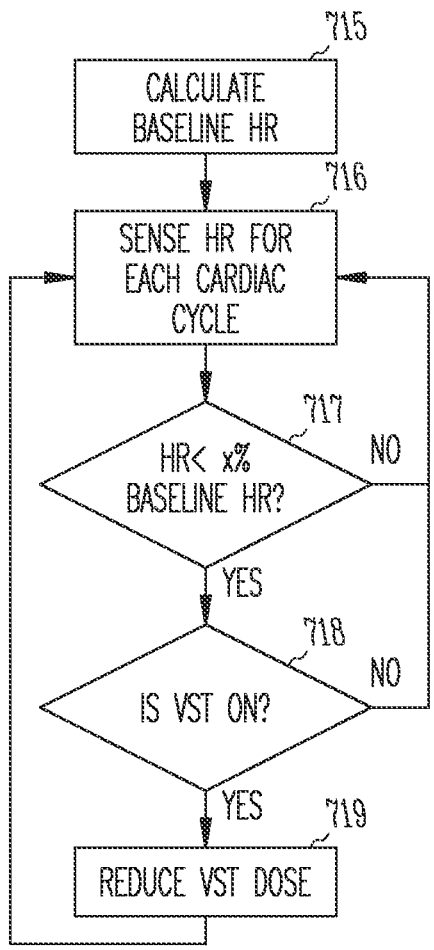
FIGS. 7-9 illustrate VST titration algorithms for a closed loop system, according to various embodiments.
Figure 8:
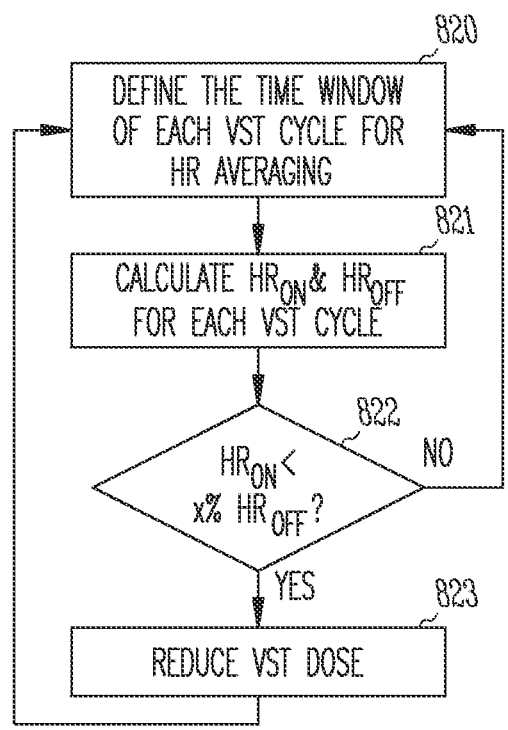
Figure 9:
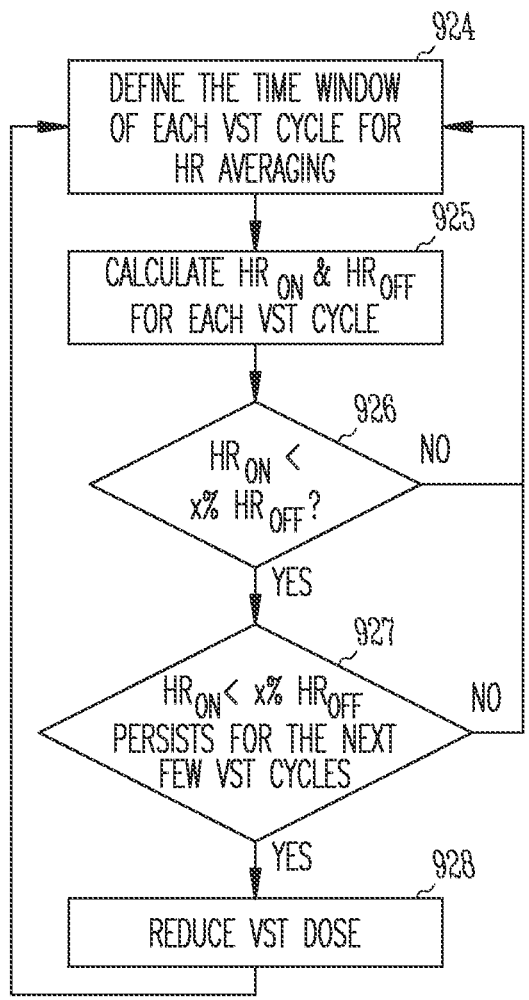

FIGS. 7-9 illustrate VST titration algorithms for a closed loop system, according to various embodiments. An embodiment of a closed loop system includes neural stimulation electrodes and intracardiac sensing electrodes. Various closed loop system embodiments are able to monitor the heart rate lowering effects, or lack thereof, and automatically adjust the parameters. Some embodiments are capable of adjusting parameters for each VST cycle.

Some closed loop system embodiments average heart rate data for a VST cycle when VST is ON, average heart rate data for the VST cycle when VST is OFF, and compare the VST ON heart rate average to the VST OFF heart rate average less a certain time offset to avoid any transient or residual effects. If heart rate drops to a certain degree during the vagal stimulation, the parameters are adjusted to lower VST dose for the next VST stimulus.

An example of a titration algorithm for a closed loop system will compare heart rate with a baseline heart rate (e.g. hourly averaged HR) for each cardiac cycle. If the heart rate during VST is below the baseline value, the VST dose is reduced. Some embodiments use an accelerometer or minute ventilation (MV) sensor to sense exercise activity, and turn VST OFF or lower the VST intensity or lower the upper boundary for the VST intensity during exercise to improve exercise tolerance.

FIG. 7 illustrates an embodiment of a VST titration algorithm for a closed loop system. At 715, a baseline heart rate is calculated. The heart rate can be averaged for a certain time window. By way of example, the baseline heart rate can be averaged hourly and updated hourly. Other schedules for averaging and updating the baseline heart rate data can be used. Some embodiments determine the appropriate heart rate for various states (e.g. sleeping, awake and resting, awake and moving, awake and exercising). The limit for bradycardia (i.e. the degree of bradycardia permitted during VST) is programmable. Heart rate is sensed at 716. For example, heart rate can be sensed for each cardiac cycle. The sensed heart rate is compared to the baseline heart rate to determine if a bradycardia event (determined by the programmable limit) during the ON time of VST cycle. For example, a bradycardia event is detected if the sensed heart rate is less than a percentage (or offset) from a baseline heart rate, as illustrated at 717, and if the VST is ON, as illustrated at 718. A detected bradycardia event triggers an automatic reduction of VST dose, as illustrated at 719. The automatic reduction of VST dose may be in programmed incremental steps, or may be based on the amount that the heart rate is below the baseline heart rate.

FIG. 8 provides another illustration of an embodiment of a VST titration algorithm for a closed loop system. The average heart rate during VST ON/OFF cycle is calculated during the end of the respective cycle (e.g. last 5 seconds during the ON or OFF cycle) to avoid any transitional or residual effects of the heart rate response. The time window for HR averaging for each VST ON/OFF cycle could be preprogrammed, as illustrated at 820. The limit for bradycardia is programmable (the degree of bradycardia permitted during VST). At 821, the average heart rate during VST ON and the average heart rate during VST OFF is calculated for each VST cycle. The average heart rate during VST ON is compared to the average heart rate compared during the VST OFF, as illustrated at 822, to determine if a bradycardia event occurred. A bradycardia event automatically reduces the VST dose, as illustrated at 823. The automatic reduction of VST dose may be in programmed incremental steps, or may be based on the amount that the heart rate is below the baseline heart rate.

FIG. 9 provides another illustration of an embodiment of a VST titration algorithm for a closed loop system. The illustrated process involves determining whether bradycardia condition is occurring for each cycle, and whether the bradycardia condition consists for a predetermined number of cycles. If the bradycardia condition is persistent over a few cycles, a bradycardia event is determined to be occurring and VST intensity is automatically adjusted. A time window for averaging heart rate is preprogrammed at 924.

At 925, the average heart rate during VST ON and the average heart rate during VST OFF is calculated for each VST cycle. The average heart rate during VST ON is compared to the average heart rate compared during the VST OFF, as illustrated at 926, to determine if a bradycardia condition occurred. At 927, it is determined if the bradycardia condition persists for a determined amount of VST cycles. If the bradycardia condition is persistent, a bradycardia event is determined to be occurring and, as illustrated at 928, the VST dose is automatically reduced. The automatic reduction of VST dose may be in programmed incremental steps, or may be based on the amount that the heart rate is below the baseline heart rate.

Some embodiments use a physical activity sensor (such as an accelerometer or minute ventilation sensor) and control the VST intensity to appropriately account for sensed physical activity. For example, VST can be turned off during exercise to enhance exercise tolerance. Some embodiments use a timer and a programmed schedule to adjust VST intensity. For example, more VST intensity may be delivered during usual sleep times than during normal work times.

It is believed that these algorithms enhance VST delivery by preventing significant heart rate reductions which may cause a patient to feel worse and may limit their exercise performance. Thus, preventing heart rate reductions is expected to significantly improve the tolerability of VST. Additionally, lower VST intensity reduces other side effects associated with a high stimulation output, such as coughing, pain, etc., and prolongs battery life of the VST stimulation device.

VST for treating various myocardial conditions can be integrated with various myocardial stimulation therapies. The integration of therapies may have a synergistic effect. Therapies can be synchronized with each other, and sensed data can be shared. A myocardial stimulation therapy provides a cardiac therapy using electrical stimulation of the myocardium. Some examples of myocardial stimulation therapies are provided below.

A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhthmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

Figure 10:
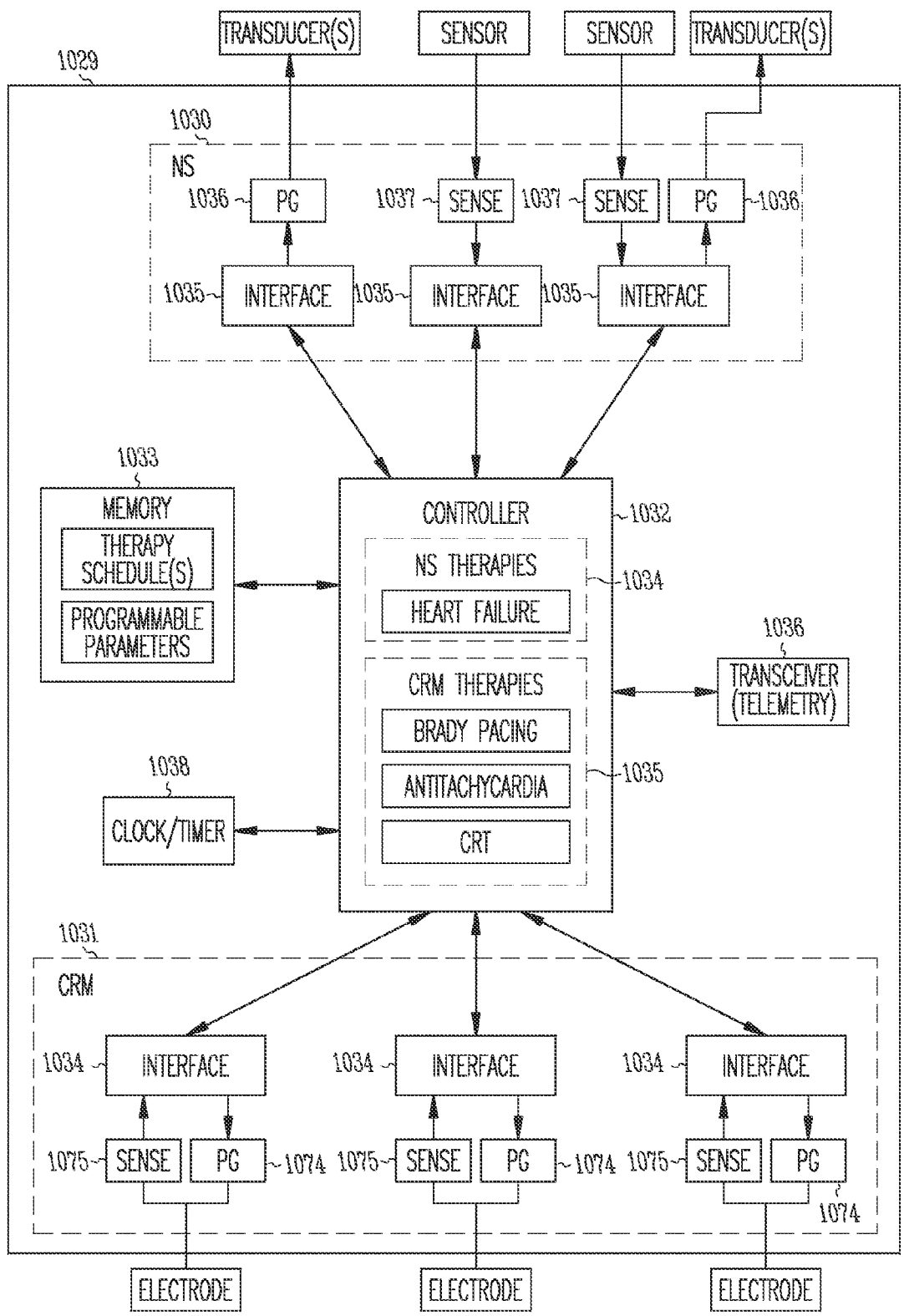
FIG. 10 illustrates an implantable medical device (IMD) having neural stimulation and cardiac rhythm management functions, according to various embodiments of the present subject matter.

FIG. 10 illustrates an implantable medical device (IMD) 1029 having a neural stimulation (NS) component 1030 and a cardiac rhythm management (CRM) component 1031 according to various embodiments of the present subject matter. The illustrated device includes a controller 1032 and memory 1033. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. For example, therapy schedule(s) and programmable parameters can be stored in memory. According to various embodiments, the controller includes a processor to execute instructions embedded in memory to perform the neural stimulation and CRM functions. The illustrated neural stimulation therapy 1034 can include VST, such as VST to treat heart failure or other cardiovascular disease. Various embodiments include CRM therapies 1035, such as bradycardia pacing, anti-tachycardia therapies such as ATP, defibrillation and cardioversion, and cardiac resynchronization therapy (CRT). The illustrated device further includes a transceiver 1036 and associated circuitry for use to communicate with a programmer or another external or internal device. Various embodiments include a telemetry coil.

The CRM therapy section 1031 includes components, under the control of the controller, to stimulate a heart and/or sense cardiac signals using one or more electrodes. The illustrated CRM therapy section includes a pulse generator 1074 for use to provide an electrical signal through an electrode to stimulate a heart, and further includes sense circuitry 1075 to detect and process sensed cardiac signals. An interface 1034 is generally illustrated for use to communicate between the controller 1032 and the pulse generator 1074 and sense circuitry 1075. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 1030 includes components, under the control of the controller, to stimulate a neural stimulation target and/or sense parameters associated with nerve activity or surrogates of nerve activity such as heart rate, blood pressure, respiration. Three interfaces 1035 are illustrated for use to provide neural stimulation. However, the present subject matter is not limited to a particular number interfaces, or to any particular stimulating or sensing functions. Pulse generators 1036 are used to provide electrical pulses to transducer/electrode or transducers/electrodes for use to stimulate a neural stimulation target. According to various embodiments, the pulse generator includes circuitry to set, and in some embodiments change, the amplitude of the stimulation pulse, the pulse width of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 1037 are used to detect and process signals from a sensor, such as a sensor of nerve activity, heart rate, blood pressure, respiration, and the like. Sensor(s) may be used to sense laryngeal vibration. Sensor (s) may be used to detect a state (e.g. accelerometer used to detect activity). The interfaces 1034 are generally illustrated for use to communicate between the controller 1032 and the pulse generator 1036 and sense circuitry 1037. Each interface, for example, may be used to control a separate lead. Various embodiments of the NS therapy section only includes a pulse generator to stimulate a neural target. The illustrated device further includes a clock/timer 1038, which can be used to deliver the programmed therapy according to a programmed stimulation protocol and/or schedule.

Figure 11:
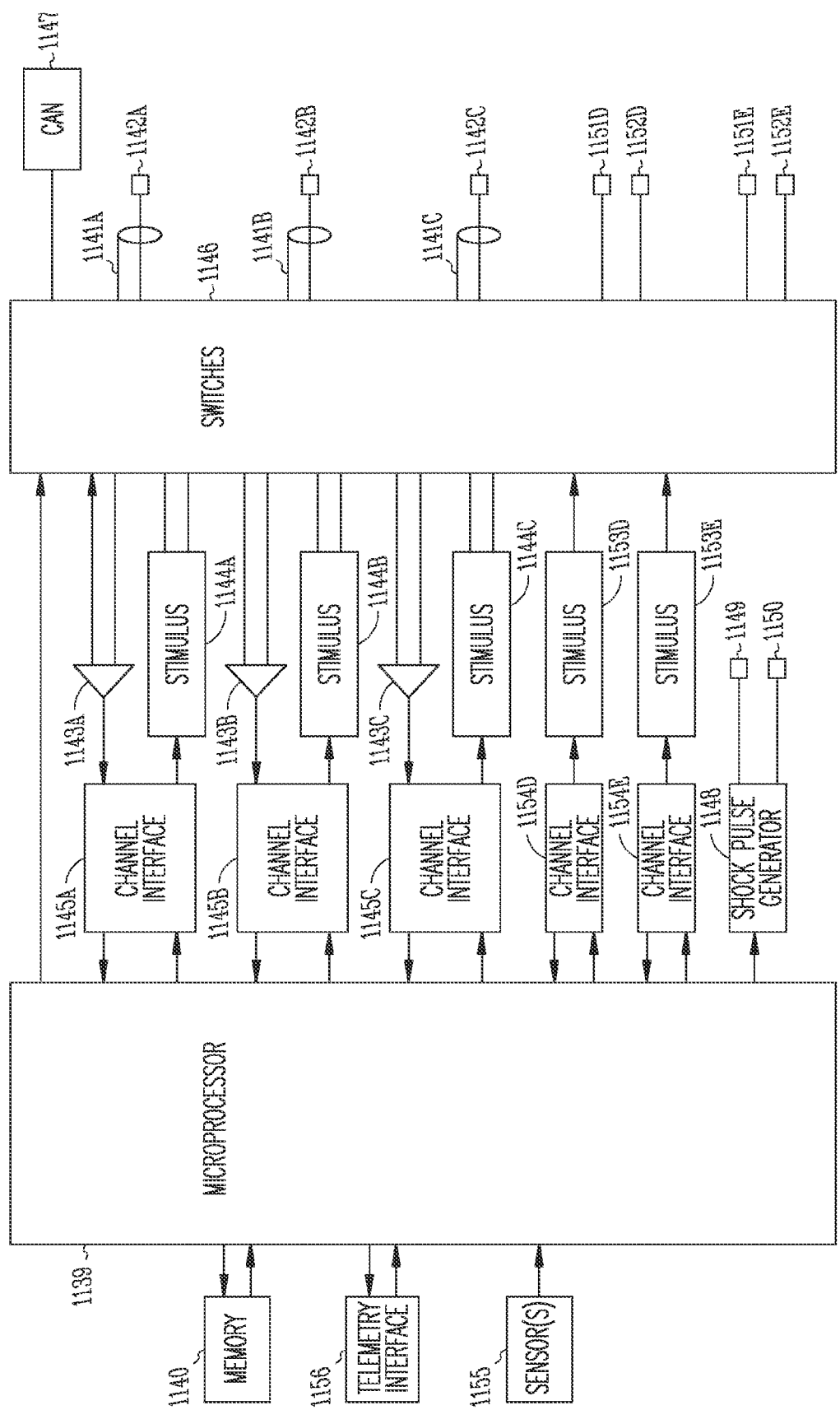
FIG. 11 shows a system diagram of an embodiment of a microprocessor-based implantable device, according to various embodiments.

FIG. 11 shows a system diagram of an embodiment of a microprocessor-based implantable device, according to various embodiments. The controller of the device is a microprocessor 1139 which communicates with a memory 1140 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1141A-C and tip electrodes 1142A-C, sensing amplifiers 1143A-C, pulse generators 1144A-C, and channel interfaces 1145A-C. Each channel thus includes a pacing channel made up of the pulse generator connected to the electrode and a sensing channel made up of the sense amplifier connected to the electrode. The channel interfaces 1145A-C communicate bidirectionally with the microprocessor 1139, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 1146 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1147 or an electrode on another lead serving as a ground electrode. A shock pulse generator 1148 is also interfaced to the controller for delivering a defibrillation shock via shock electrodes (e.g. electrodes 1149 and 1150) to the atria or ventricles upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 1151D and a second electrode 1152D, a pulse generator 1153D, and a channel interface 1154D, and the other channel includes a bipolar lead with a first electrode 1151E and a second electrode 1152E, a pulse generator 1153E, and a channel interface 1154E. Other embodiments may use unipolar leads in which case the neural stimulation pulses are referenced to the can or another electrode. Other embodiments may use tripolar or multipolar leads. In various embodiments, the pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links. Sensor(s) 1155 are used by the microprocessor 1139 efficacy of therapy (e.g. blood pressure) and/or detect events (e.g. laryngeal vibration) or states (e.g. activity sensors).

The figure illustrates a telemetry interface 1156 connected to the microprocessor, which can be used to communicate with an external device. The illustrated microprocessor 1139 is capable of performing neural stimulation therapy routines and myocardial (CRM) stimulation routines. Examples of NS therapy routines include VST therapies to provide myocardial therapies. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

Figure 12:
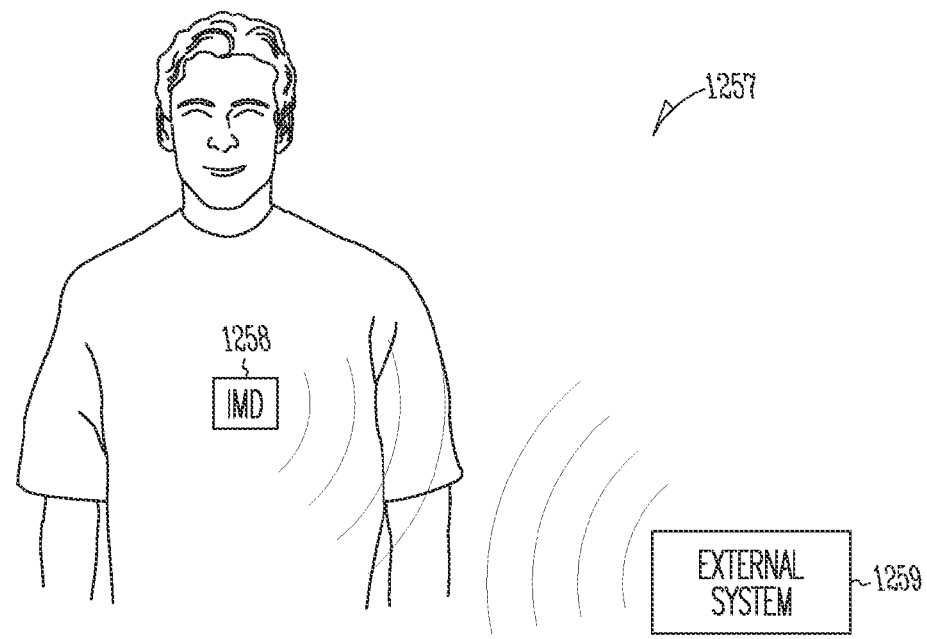
FIG. 12 illustrates a system including an implantable medical device (IMD) and an external system or device, according to various embodiments of the present subject matter.

FIG. 12 illustrates a system 1257 including an implantable medical device (IMD) 1258 and an external system or device 1259, according to various embodiments of the present subject matter. Various embodiments of the IMD include NS functions or include a combination of NS and CRM functions. The IMD may also deliver biological agents and pharmaceutical agents. The external system and the IMD are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. According to various embodiments, the IMD provides VST with a relatively low intensity that remains therapeutically effective for cardiovascular diseases such as heart failure therapy and that is low enough to not induce changes.

The external system allows a user such as a physician or other caregiver or a patient to control the operation of the IMD and obtain information acquired by the IMD. In one embodiment, the external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below.

The telemetry link provides for data transmission from the implantable medical device to the external system. This includes, for example, transmitting real-time physiological data acquired by the IMD, extracting physiological data acquired by and stored in the IMD, extracting therapy history data stored in the IMD, and extracting data indicating an operational status of the IMD (e.g., battery status and lead impedance). The telemetry link also provides for data transmission from the external system to the IMD. This includes, for example, programming the IMD to acquire physiological data, programming the IMD to perform at least one self-diagnostic test (such as for a device operational status), and programming the IMD to deliver at least one therapy.

Figure 13:
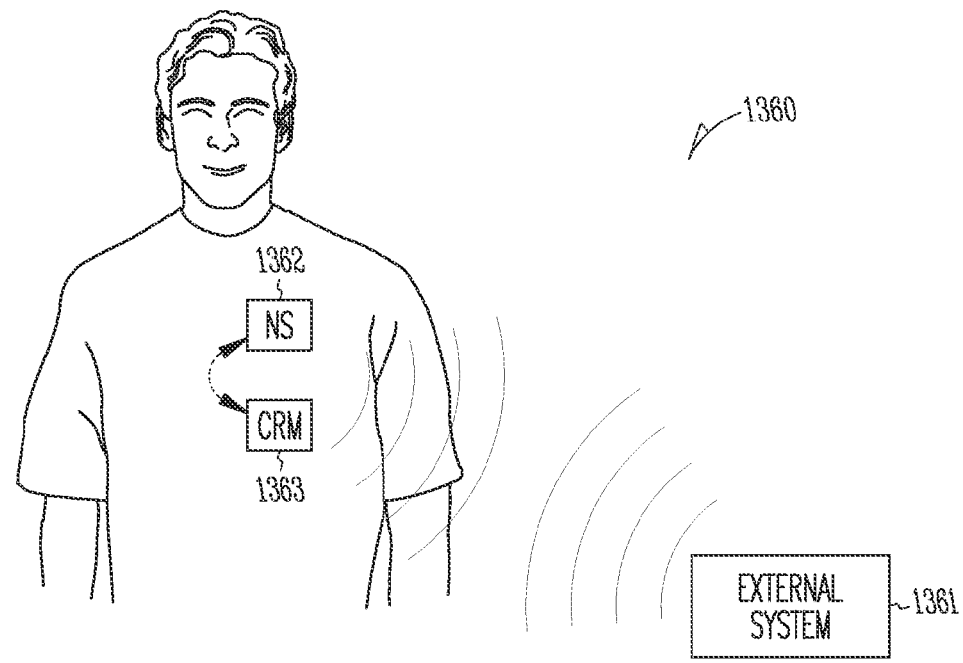
FIG. 13 illustrates a system including an external device, an implantable neural stimulator (NS) device and an implantable cardiac rhythm management (CRM) device, according to various embodiments of the present subject matter.

FIG. 13 illustrates a system 1360 including an external device 1361, an implantable neural stimulator (NS) device 1362 and an implantable cardiac rhythm management (CRM) device 1363, according to various embodiments of the present subject matter. Various aspects involve a method for communicating between an NS device and a CRM device or other cardiac stimulator. In various embodiments, this communication allows one of the devices 1362 or 1363 to deliver more appropriate therapy (i.e. more appropriate NS therapy or CRM therapy) based on data received from the other device. Some embodiments provide on-demand communications. In various embodiments, this communication allows each of the devices to deliver more appropriate therapy (i.e. more appropriate NS therapy and CRM therapy) based on data received from the other device. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device. In some embodiments, the external system functions as a communication bridge between the NS and CRM devices.

Figure 14:
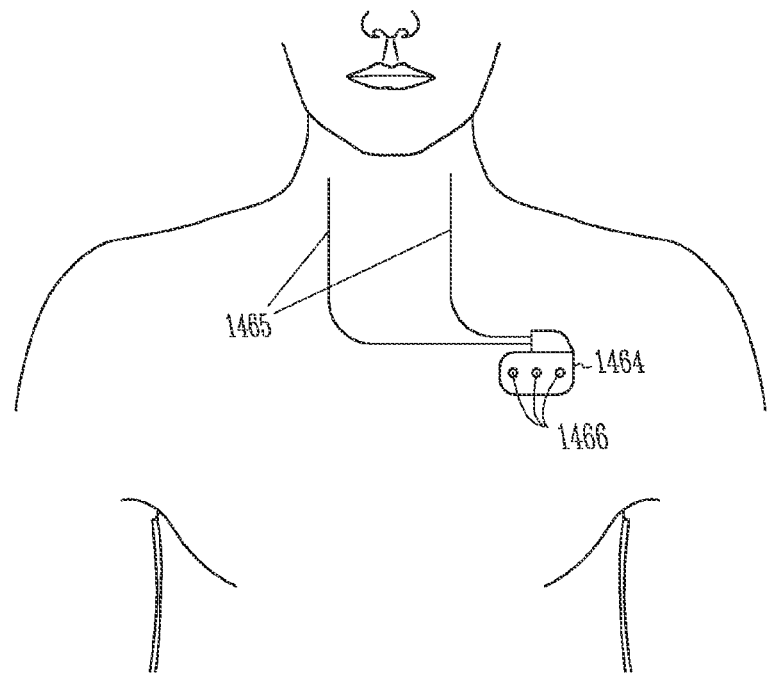
FIGS. 14-15 illustrate system embodiments adapted to provide VST, and are illustrated as bilateral systems that can stimulate both the left and right vagus nerve.
Figure 15:
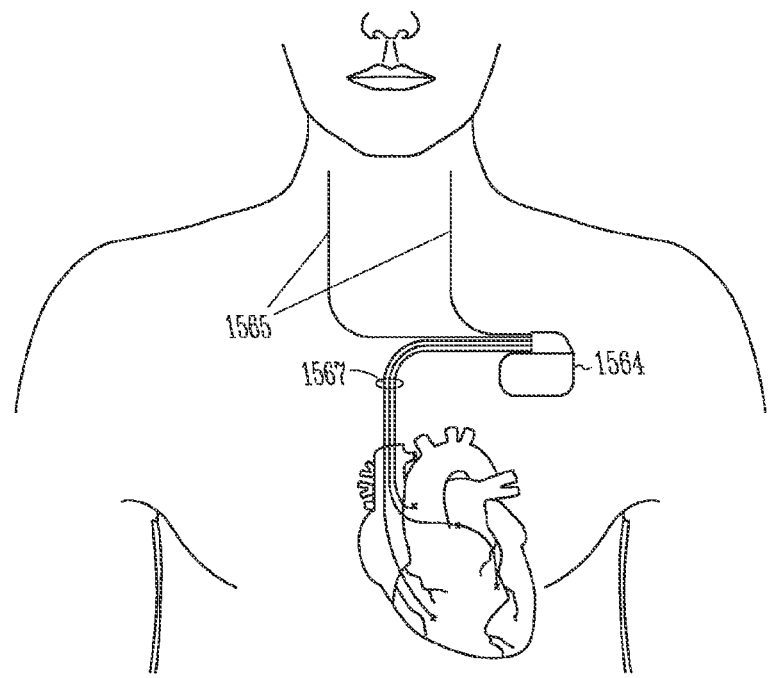

FIGS. 14-15 illustrate system embodiments adapted to provide VST, and are illustrated as bilateral systems that can stimulate both the left and right vagus nerve. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves. The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve. FIGS. 14-15 illustrate the use of a lead to stimulate the vagus nerve. Wireless technology could be substituted for the leads, such that a leadless electrode is adapted to stimulate a vagus nerve and is further adapted to wirelessly communicate with an implantable system for use in controlling the VST.

FIG. 14 illustrates a system embodiment in which an IMD 1464 is placed subcutaneously or submuscularly in a patient's chest with lead(s) 1465 positioned to stimulate a vagus nerve. According to various embodiments, neural stimulation lead(s) 1465 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The neural targets can be stimulated using other energy waveforms, such as ultrasound and light energy waveforms. The illustrated system includes leadless ECG electrodes 1466 on the housing of the device. These ECG electrodes are capable of being used to detect heart rate, for example.

FIG. 15 illustrates an IMD 1564 placed subcutaneously or submuscularly in a patient's chest with lead(s) 1567 positioned to provide a CRM therapy to a heart, and with lead(s) 1565 positioned to stimulate and/or inhibit neural traffic at a neural target, such as a vagus nerve, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 16:
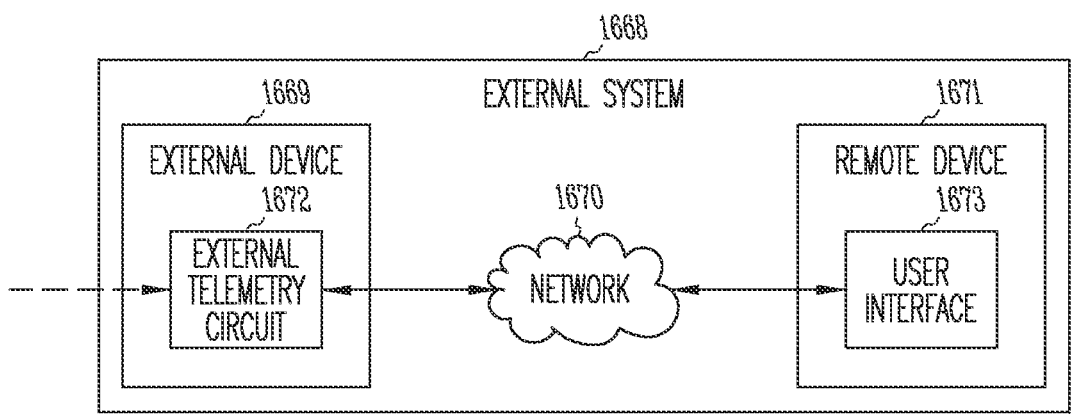
FIG. 16 is a block diagram illustrating an embodiment of an external system.

FIG. 16 is a block diagram illustrating an embodiment of an external system 1668. The external system includes a programmer, in some embodiments. In the illustrated embodiment, the external system includes a patient management system. As illustrated, the external system is a patient management system including an external device 1669, a telecommunication network 1670, and a remote device 1671. The external device 1669 is placed within the vicinity of an implantable medical device (IMD) and includes an external telemetry system 1672 to communicate with the IMD. The remote device(s) is in one or more remote locations and communicates with the external device through the network, thus allowing a physician or other caregiver to monitor and treat a patient from a distant location and/or allowing access to various treatment resources from the one or more remote locations. The illustrated remote device includes a user interface 1673. According to various embodiments, the external device includes a neural stimulator, a programmer or other device such as a computer, a personal data assistant or phone. The external device, in various embodiments, includes two devices adapted to communicate with each other over an appropriate communication channel, such as a computer by way of example and not limitation. The external device can be used by the patient or physician to provide feedback indicative of laryngeal vibration or patient discomfort, for example.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by one or more processors cause the processor(s) to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system, comprising:
a patient-operable external controller configured to transmit a signal associated with a titration command; and
an implantable neurostimulator configured to receive the signal, the implantable neurostimulator comprising:
a pulse generator configured to deliver, through at least one electrode configured to be operably positioned proximate to a cervical vagus nerve, a therapy including continuously-cycling, intermittent and periodic pulses delivered at an intensity that avoids acute physiological side effects and with an unchanging cycle not triggered by physiological markers in a manner that non-selectively stimulates both afferent axons and efferent axons in the cervical vagus nerve of a patient; and
a memory configured to store instructions for titrating the intensity of the electrical pulses including instructions for titrating one or more pulse parameters selected from the group consisting of an amplitude, a pulse width and a pulse frequency and instructions for preventing titration of the intensity by titration of one or more pulse parameters selected from the group consisting of an amplitude, a pulse width and a pulse frequency from exceeding an upper bound for the intensity, wherein the implantable neurostimulator includes processing circuitry configured to operate on the instructions to titrate the intensity of the electrical pulses in response to the signal associated with the titration command.

2. The system of claim 1, further comprising:
an external programmer operable by a healthcare professional and configured to program the instructions into the memory.

3. The system of claim 2, wherein the external programmer is further configured to receive at least one set of predefined stimulation parameters.

4. The system of claim 3, wherein the external programmer is further operable by the healthcare professional to modify at least one parameter of the at least one set of predefined stimulation parameters based on the patient's physiological requirements.

5. The system of claim 1, wherein the external controller is configured to transmit instructions to promote patient-tolerability to the therapy.

6. The system of claim 5, wherein the system is configured to decrease the intensity to maintain patient-tolerability.

7. The system of claim 5, wherein:
the intensity of the delivered electrical therapeutic stimulation comprises one or more parameters comprising an amplitude, frequency, duty cycle, and pulse width;
the instructions are further configured to increase one of the parameters upon receipt of the signal associated with the titration command; and
upon receipt of the unique signal indicating that the increased intensity of the electrical therapeutic stimulation is not tolerable to the patient, decreasing the increased parameter and increasing another one of the parameters.

8. The system of claim 1, wherein instructions include a schedule for the therapy.

9. The system of claim 8, wherein the external controller is configured to allow the patient to control the implantable neural stimulator.

10. The system of claim 8, wherein the predefined schedule comprises a period of time during which the intensity is titrated.

11. The system of claim 1, wherein the external controller is configured to wirelessly communicate with the implantable neurostimulator.

12. The system of claim 11, wherein the system is configured to provide battery status to the external controller.

13. The system of claim 1, wherein the intensity is further titrated by modifying a duty cycle of the pulses.

14. The system of claim 1, wherein the electrode includes an electrode configured to surround the vagus nerve.

15. The system of claim 14, wherein the electrode includes a nerve cuff electrode.

16. The system of claim 1, wherein the electrode includes an intravascular electrode, the implantable neurostimulator configured to use the intravascular electrode to transvascularly stimulate the cervical vagus nerve.

17. The system of claim 1, wherein the therapy includes a therapy for a chronic cardiac condition.

18. The system of claim 17, wherein the therapy includes a heart failure therapy.

19. A system, comprising:
a patient-operable external controller configured to transmit a signal associated with a titration command; and
an implantable neurostimulator comprising:
a pulse generator configured to deliver, through at least one electrode configured to surround a cervical vagus nerve, a therapy for a chronic cardiac condition, wherein the therapy includes continuously-cycling, intermittent and periodic pulses delivered according to a stimulation schedule in a manner that non-selectively stimulates both afferent axons and efferent axons in the cervical vagus nerve of a patient;
a memory configured to store instructions for titrating the intensity of the electrical pulses including instructions for titrating one or more pulse parameters selected from the group consisting of an amplitude, a pulse width and a pulse frequency and instructions for preventing titration of the intensity by titration of one or more pulse parameters selected from the group consisting of an amplitude, a pulse width and a pulse frequency from exceeding an upper bound for the intensity, wherein the implantable neurostimulator includes processing circuitry configured to operate on the instructions to titrate the intensity of the electrical pulses in response to the signal associated with the titration command.

20. The system of claim 19, wherein the upper bound prevents therapy from being delivered at an intolerable intensity.

* * * * *